US012672633B2

(12) United States Patent
Collier

(10) Patent No.: US 12,672,633 B2
(45) Date of Patent: Jul. 7, 2026

(54) HYBRID TOMATO VARIETY 'H2249'

(71) Applicant: H.J. HEINZ COMPANY BRANDS LLC, Pittsburgh, PA (US)

(72) Inventor: George Collier, Wheatley (CA)

(73) Assignee: H.J. HEINZ COMPANY BRANDS LLC, Pittsburgh, PA (US)

( * ) Notice: Subject to any disclaimer, the term of this patent is extended or adjusted under 35 U.S.C. 154(b) by 510 days.

(21) Appl. No.: 18/087,272

(22) Filed: Dec. 22, 2022

(65) Prior Publication Data
US 2024/0206418 A1     Jun. 27, 2024

(51) Int. Cl.
*A01H 5/08*     (2018.01)
*A01H 1/00*     (2006.01)
*A01H 6/82*     (2018.01)

(52) U.S. Cl.
CPC ............... *A01H 6/825* (2018.05); *A01H 1/00* (2013.01); *A01H 5/08* (2013.01)

(58) Field of Classification Search
None
See application file for complete search history.

(56)     References Cited

U.S. PATENT DOCUMENTS 10,602,711 B2     3/2020   Ozminkowski, Jr.
2021/0185971 A1*  6/2021   Ozminkowski, Jr. .... A01H 5/08

OTHER PUBLICATIONS

"Applying for a Plant Variety Certificate of Protection", USDA, https://www.ams.usda.gov/services/pv po/application-help/apply, downloaded May 1, 2023.*
UPOV, Explanatory Notes on Essentially Derived Varieties Under the 1991 Act of the UPOV Convention, Apr. 6, 2017.*
Ex Parte C, USPQ 2d 1492 (1992).*
Ex Parte McGowen Board Decision in U.S. Appl. No. 14/996,093, decided Jun. 15, 2020.*
Y: Haun et al., Plant Physiology, Feb. 2011, vol. 155, pp. 645-655.*
Z: Großkinsky et al., J. Exp. Bot., vol. 66, No. 11, pp. 5429-5440, 2015.*

* cited by examiner

*Primary Examiner* — Phuong T Bui
(74) *Attorney, Agent, or Firm* — FITCH EVEN TABIN & FLANNERY, LLP

(57)     ABSTRACT

Hybrid tomato variety 'H2249' is described. The tomato variety is a ground-culture hybrid processing tomato variety suitable for the dual use market with both hand and machine harvest and is adaptable to humid climactic regions such as the Northeastern USA, Portugal and Italy. It is a late season variety with resistance to *Verticillium* wilt, *Fusarium* wilt races 1 and 2, root knot nematode, tomato spotted wilt virus, bacterial speck, late blight and moderate tolerance to bacterial spot and early blight.

17 Claims, 2 Drawing Sheets
(2 of 2 Drawing Sheet(s) Filed in Color)

HYBRID TOMATO VARIETY 'H2249'

FIELD

This disclosure relates to the field of plant breeding. In particular, this disclosure relates to a new variety of tomato, *Solanum lycopersicum* variety denominated 'H2249'.

BACKGROUND

Breeding improved tomato varieties involves providing genetics that give an advantage to the grower, processor, consumer, or other members of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most tomato varieties for commercial processing are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining resistance to *Verticillium* wilt race 1 (*Verticillium* dahlia), *Fusarium* wilt races 1 and 2 (*Fusarium oxysporum* pv *lycopersici*) and root knot nematode (*Meloidogyne incognita*) are highly desirable in most climates around the world. Humid growing climates, such as the Northeastern United States have pressure from bacterial and fungal pathogens. Frequent outbreaks of bacterial spot (*Xanthomonas* spp.), bacterial canker (*Clavibacter michiganensis*) and early blight (*Alternaria solani*) can occur. Thus, varieties with resistance are in high demand by both growers and processors to ensure a productive crop cycle.

Processing tomato quality parameters differ from those of fruit used in the fresh market. The processing characteristics are typically determined using a sample of hot-break tomato pulp or juice produced in a consistent manner to those familiar with the art. For example, a fixed mass of tomatoes may be cooked in a microwave oven for several minutes to halt any enzymatic breakdown of the sample, lost water is replaced, and the sample is pulped to remove skins and seed to produce a uniform juice sample. The juice sample can be analyzed for various quality parameters important to processing tomato including but not limited to gross viscosity measures such as juice Bostwick, soluble solids measures using a refractometer (° Brix), measures of acidity and pH, and measures of color (e.g., a Hunter a/b score). The value of these traits depends on the product that is being commercially produced by the processing factory. In some instances, a factory will put a higher value on a thick viscosity variety, whereas in other instances, a thin viscosity will make a superior product and is preferred.

SUMMARY

Provided herein is a new and distinct tomato variety named 'H2249' that produces good field yields of very large fruit and is best adapted to humid environments such as the Midwestern US and Italy. The variety 'H2249' has resistance to *Verticillium* wilt race 1, *Fusarium* wilt races 1 and 2, root knot nematode, bacterial speck, tomato spotted wilt virus and late blight. 'H2249' has also demonstrated a modest level of tolerance to both bacterial spot and early blight. The fruit of 'H2249' have average red color and an average fruit weight of 120 grams. 'H2249' presents an advantage over industry standard varieties such as 'H1015' by adding resistant to tomato spotted wilt virus, late blight and significantly larger fruit size.

In one aspect, the present disclosure is directed to a tomato plant, as well as any plant part or portion isolated therefrom, produced by growing 'H2249' tomato seed. In another aspect, the present disclosure is directed to a tomato plant or part isolated therefrom having all the physiological, morphological, and/or genetic characteristics of a tomato plant produced by growing 'H2249' tomato seed having ATCC Accession Number PTA-127484. In yet another aspect, the present disclosure is directed to a tomato plant having all of the physiological and morphological characteristics of tomato variety 'H2249', and specifically including those listed in Table 1 below, wherein representative seed is deposited under ATCC Accession Number PTA-127484.

In still another aspect, the present disclosure is directed to tomato seed having at least a first set of the chromosomes of tomato variety 'H2249', wherein representative seed is deposited under ATCC Accession Number PTA-127484. In another aspect, the present disclosure is directed to an $F_1$ hybrid tomato seed, methods of making $F_1$ hybrid tomato seed, plants grown from the seed, leaf, ovule, pollen, rootstock, scion, fruit, cotyledon, meristem, anther, root, root tip, pistil, flower, stem, calli, stalk, hypocotyl, pericarp, or portion thereof isolated therefrom having 'H2249' as a parent, wherein 'H2249' is grown from 'H2249' tomato seed having ATCC Accession Number PTA-127484. The disclosure is also directed to a method of producing a tomato plant derived from tomato variety 'H2249', including crossing a plant of tomato variety 'H2249' with another tomato plant. The method may further comprise harvesting seed from the $F_1$ hybrid tomato seed and/or crossing the $F_1$ hybrid tomato plant with itself or another plant to produce seed from a progeny plant.

Tomato plant parts include leaf, ovule, pollen, rootstock, scion, fruit, cotyledon, meristem, anther, root, root tip, pistil, flower, stem, calli, stalk, hypocotyl, pericarp, the like, and any portion thereof. In another embodiment, the present disclosure is further directed to tomato fruit, stem, leaf, root, root tip, pollen, rootstock, scion, ovule, seed, and flower, and any portion thereof, isolated from 'H2249' tomato plants. In one aspect, the plant part comprises at least one cell from tomato variety 'H2249'. In another aspect, the present disclosure is further directed to tissue culture of regenerable cells derived from 'H2249' tomato plants. In one aspect, the tissue culture of regenerable cells has all the physiological and morphological characteristics of tomato variety 'H2249'. The disclosure is further directed to a tomato plant regenerated from tissue culture. In another aspect, the disclosure is directed to a protoplast produced from tissue culture and a plant regenerated from the protoplast. At least in some approaches, the plant regenerated from the tissue culture or protoplast has all of the physiological and morphological characteristics of tomato variety 'H2249', and specifically including those listed in Table 1.

In another aspect, the disclosure is directed to a method for producing a plant part, which at least in one aspect is tomato fruit, and harvesting the plant part. In another aspect, the plant part comprises at least one cell from tomato variety 'H2249'.

The disclosure also is directed to vegetatively propagating a plant of tomato variety 'H2249' by obtaining a part of the plant and regenerating a plant from the plant part. At least in some approaches, the regenerated plant has all of the physiological and morphological characteristics of tomato variety 'H2249', and specifically including those listed in Table 1.

In yet another aspect, the present disclosure is further directed to a method of selecting tomato plants by a) growing 'H2249' tomato plants wherein the 'H2249' plants are grown from tomato seed having ATCC Accession Number PTA-127484; and b) selecting a plant from step a). In another aspect, the present disclosure is further directed to tomato plants, plant parts, and seeds produced by the tomato plants, where the tomato plants are isolated by the selection method.

In another aspect, the present disclosure is further directed to a method of breeding tomato plants by crossing a tomato plant with a plant grown from 'H2249' tomato seed having ATCC Accession Number PTA-127484. In another aspect, the tomato plant of tomato variety 'H2249' is self-pollinated. In still another aspect, the present disclosure is further directed to tomato plants, tomato parts from the tomato plants, and seeds produced therefrom where the tomato plant is isolated by the breeding method.

In another aspect, the disclosure relates to a plant of tomato variety 'H2249' comprising a transgene and/or a single locus conversion, and any seeds or plant parts isolated therefrom. The disclosure also relates to methods for preparing a plant of tomato variety 'H2249' comprising a transgene and/or a single locus conversion. In one aspect, the plant comprising a single locus conversion and/or transgene has all the physiological and morphological characteristics of tomato variety 'H2249'.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION

Figure 1:
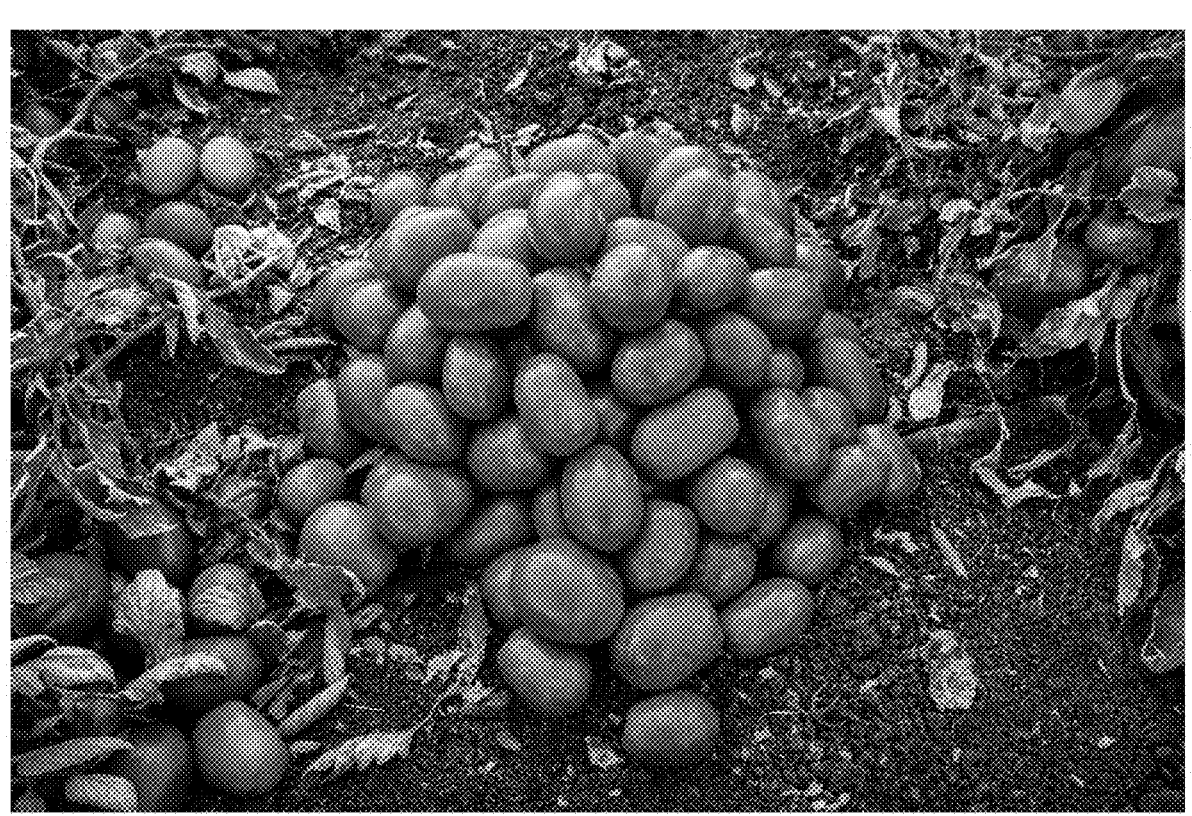
FIG. 1 illustrates the fruit of tomato variety 'H2249'.
Figure 2:
FIG. 2 illustrates the fruit and plant of tomato variety 'H2249'.

Described herein is the new and distinct tomato variety named 'H2249' that was developed to provide a ground-culture hybrid tomato variety (i.e., not grown on stakes) that is suitable for machine harvest and are adaptable to the climactic conditions of regions such as the Northeastern United States.

Processing tomato varieties combining resistance to *Verticillium* wilt race 1 (*Verticillium* dahlia), *Fusarium* wilt race 1 and 2 (*Fusarium oxysporum* pv. *lycopersici*), root knot nematode (*Meloidogyne incognita*), bacterial spot (*Xanthomonas campestris* spp.), bacterial canker (*Clavibacter michiganensis*) and early blight (*Alternaria solani*) are highly desirable in many humid climates around the world. Varieties for processing are also valued when they are very firm and have a maturity concentrated enough to allow for machine harvesting prior to the onset of fruit rots.

Tomato plants of 'H2249' are resistant to *Verticillium* wilt race 1, *Fusarium* wilt races 1 and 2, root knot nematode, bacterial speck, tomato spotted wilt virus and late blight. Moderate tolerance is bacterial spot and early blight is also found in the variety 'H2249'. Plants have a small vine, late maturity and a very compact growing habit as compared to tomato varieties of the same market class. Fruit of 'H2249' are extremely large (120 grams) and meaty with average color, making the variety suitable for both processing and dual-use markets.

Development of Variety 'H2249'

The original parental lines used to produce tomato variety 'H2249' are as follows: the female parent is proprietary breeding line 'h38319', and the male parent is proprietary breeding line 'h37620'. Tomato variety 'H2249' is an $F_1$ hybrid of the two parental lines. There are no other known designations for 'h38319' or 'h37620', and there are no other known designations for variety 'H2249'.

The parental lines 'h38319' and 'h37620' are both homozygous and have been determined to be uniform. Each parental line was developed using a modified pedigree breeding method that included a combination of individual plant selections from segregating populations and bulking of progeny.

Tomato variety 'H2249' was chosen from the first filial generation and is heterozygous.

Stability of Variety 'H2249'

The variety is uniform and stable within commercially acceptable limits. As is true with other tomato varieties, a small percentage of variants can occur within commercially acceptable limits for almost any characteristic during the course of repeated multiplication. However, no variants were observed during the three years in which the variety was observed to be uniform and stable.

TABLE 1

| Characterization of tomato variety 'H2249' compared to two processing industry standards, 'H1015' and 'H3402' | | | |
| --- | --- | --- | --- |
| Character | 'H2249' | 'H1015' | 'H3402' |
| Seedling | | | |
| Anthocyanin in hypocotyl | Present | Present | Present |
| Habit of 3-4 Wk seedling | Normal | Normal | Normal |
| Mature Plant | | | |
| Height (cm) | 83 cm | 119 cm | 109 cm |
| Growth Type | Determinate | Determinate | Determinate |
| Form | Compact | Normal | Normal |
| Size of Canopy | Small | Medium | Medium |
| Habit | Semi-erect | Sprawling | Semi-erect |

TABLE 1-continued

Characterization of tomato variety 'H2249' compared to two processing
industry standards, 'H1015' and 'H3402'

| Character | 'H2249' | 'H1015' | 'H3402' |
|---|---|---|---|
| Stem | | | |
| Branching | Profuse | Profuse | Profuse |
| Branching at Cotyledon | Absent | Absent | Absent |
| # nodes below first inflorescence | 1-4 nodes | 4-7 nodes | 7-10 nodes |
| # nodes between early inflorescence ($1^{st}$-$2^{nd}$, $2^{nd}$-$3^{rd}$) | 1-2 nodes | 1-2 nodes | 1-2 nodes |
| # nodes between later inflorescence | 1-2 nodes | 1-2 nodes | 1-2 nodes |
| Pubescence on younger stems | Sparse | Sparse | Moderate |
| Leaf | | | |
| Type | Tomato | Tomato | Tomato |
| Morphology | Compound with major and minor leaflets (image 2) | Compound with major and minor leaflets (image 2) | Compound with major and minor leaflets (image 3) |
| Margins of Major Leaflets | Shallow | Shallow | Shallow toothed |
| Marginal Rolling or Wiltiness | Strong | Moderate | Absent |
| Onset of Leaflet Rolling | Early-Season | Early season | — |
| Surface of Major Leaflets | Rugose | Rugose | Rugose |
| Pubescence | Smooth | Normal | Smooth |
| Leaf Vein Color | Transparent | Transparent | Transparent |
| Inflorescence | | | |
| Type | Simple | Forked | Simple |
| # flowers in inflorescence average | 5 | 6 | 7 |
| Leafy or "running" inflorescence | Absent | Absent | Absent |
| Flower | | | |
| Calyx | Normal | Normal | Normal |
| Calyx-Lobes | Longer than corolla | Shorter than corolla | Shorter than corolla |
| Corolla Color | Yellow | Yellow | Yellow |
| Style pubescence | Sparse | Sparse | Sparse |
| Anthers | Fused/Tubed | Fused/Tubed | Fused/Tubed |
| Fasciation | Absent | Absent | Absent |
| Fruit | | | |
| Typical shape in longitudinal section | 5 (Tapered) | 4 (Blocky Oval) | 4 (Blocky Oval) |
| Shape of transverse section | Angular | Round | Round |
| Shape of stem end | Indented | Indented | Flat |
| Shape of blossom end | Flat | Flat | Indented |
| Shape of pistil scar | Stellate | Dot | Dot |
| Abscission layer | Absent | Absent | Absent |
| point of detachment fruit at harvest | At calyx | At calyx | At calyx |
| Length of pedicel (joint to calyx attachment) (cm) | 1.7 cm | 1 cm | 1.1 cm |
| Length of mature fruit (stem axis) (cm) | 7.8 cm | 5.5 | 5.8 |
| Diameter of fruit at widest point (cm) | 6.5 cm | 4.1 | 4.5 |
| Weight of Mature Fruit (g) | 120 | 72 | 63 |
| Number of Locules | 4 | 2-4 | 2 |
| Fruit Surface | Moderate Rough | Smooth | Smooth |
| Fruit Base Color (Mature Green Stage) | Yellow-green | Medium Green | Apple/medium green |
| Fruit Pattern (mature green stage) | Uniform | Uniform | Uniform |
| Shoulder color if different from base | n/a | n/a | n/a |
| Fruit color full ripe | Red | Red | Red |
| Flesh color full ripe | Red | Red | Red |
| Flesh color | Uniform | Uniform | Uniform |
| Locular gel color of table-ripe fruit | Red | Red | Red |
| Ripening | Uniform | Uniform | Uniform |
| Stem Scar Size | Medium | Small | Small |
| Core | Coreless | Present | Coreless |
| Epidermis Color | Yellow | Yellow | Yellow |
| Epidermis | Normal | Normal | Normal |

TABLE 1-continued

| Character | 'H2249' | 'H1015' | 'H3402' |
|---|---|---|---|
| Characterization of tomato variety 'H2249' compared to two processing industry standards, 'H1015' and 'H3402' | | | |
| Epidermis Texture | Tough | Tough | Average |
| Thickness or Pericarp (mm) | 9.7 | 6.5 | 8.5 |
| Resistance to Fruit Disorder | Not tested | Not tested | Not tested |
| Disease and Pest Reactions | | | |
| Viral Diseases | | | |
| Cucumber Mosaic | n/t | n/t | n/t |
| Curly Top | n/t | n/t | n/t |
| Potato-y Virus | n/t | n/t | n/t |
| Blotch Ripening | n/t | n/t | n/t |
| Tobacco Mosaic Race 0 | n/t | n/t | n/t |
| Tobacco Mosaic Race 1 | n/t | n/t | n/t |
| Tobacco Mosaic Race 2 | n/t | n/t | n/t |
| Cracking, Concentric | n/t | n/t | n/t |
| Tobacco Mosaic Race $2^2$ | n/t | n/t | n/t |
| Tomato Spotted Wilt | Resistant | Susceptible | Susceptible |
| Tomato Yellows | n/t | n/t | n/t |
| Gold Fleck | n/t | n/t | n/t |
| Others | n/t | n/t | n/t |
| Bacterial Disease | | | |
| Bacterial Canker (*Clavibacter michiganense*) | Resistant | Resistant | Min. resistant |
| Bacterial Soft Rot (*Erwinia carotovora*) | n/t | n/t | n/t |
| Bacteria Speck race 0 (*Pseudomonas tomato*) | Resistant | Resistant | Resistant |
| Bacterial Spot (*Xanthomonas* spp) | Resistant | Susceptible | Susceptible |
| Bacterial Wilt (*Ralstonia solanacearum*) | n/t | n/t | Susceptible |
| Other Bacterial Disease | n/t | n/t | n/t |
| Fungal Disease | | | |
| Anthracnose (*Colletotrichum* spp.) | n/t | n/t | Susceptible |
| Brown Root Rot or Corky Root (*Pyrenochaeta lycopersici*) | Susceptible | n/t | Susceptible |
| Collar Rot or Stem Canker (*Alternaria solani*) | Susceptible | Susceptible | Susceptible |
| Early Blight Defoliation (*Alternaria solani*) | Resistant | Resistant | Min. resistant |
| Fusarium Wilt Race 1 (*F. oxysporum* f. *lycopersici*) | Resistant | Resistant | Resistant |
| Fusarium Wilt Race 2 (*F. oxysporum* f. *lycopersici*) | Resistant | Resistant | Resistant |
| Fusarium Wilt Race 3 (*F. oxysporum* f. *lycopersici*) | Susceptible | Susceptible | Susceptible |
| Grey Leaf Spot (*Stemphylium* spp.) | n/t | n/t | n/t |
| Late Blight, race 0 (*Phytophthora infestans*) | Resistant | Susceptible | Susceptible |
| Late Blight, race 1 | n/t | n/t | n/t |
| Leaf Mold race 1 (*Cladosporium fulvum*) | n/t | n/t | n/t |
| Leaf Mold race 2 (*Cladosporium fulvum*) | n/t | n/t | n/t |
| Leaf Mold race 3 (*Cladosporium fulvum*) | n/t | n/t | n/t |
| Leaf Mold Other Races: | n/t | n/t | n/t |
| Nail head Spot (*Alternaria tomato*) | n/t | n/t | n/t |
| Septoria Leaf spot (*S. Lycopersici*) | n/t | n/t | n/t |
| Target Leaf spot (*Corynespora cassiicola*) | n/t | n/t | n/t |
| Verticillium Wilt Race 1 (*V. dahliae* race 1) | Resistant | Resistant | Resistant |
| Verticillium Wilt Race 2 (*V. dahliae* race 2) | n/t | n/t | n/t |
| Other Fungal Disease | n/t | n/t | n/t |
| Insects and Pests | | | |
| Colorado Potato Beetle (*L. decemlineata*) | n/t | n/t | n/t |

TABLE 1-continued

| Characterization of tomato variety 'H2249' compared to two processing industry standards, 'H1015' and 'H3402' | | | |
| --- | --- | --- | --- |
| Character | 'H2249' | 'H1015' | 'H3402' |
| Root Knot Nematode (M. sp.) | Resistant | Resistant | Resistant |
| Spider Mites (*Tetranychus* spp.) | n/t | n/t | n/t |
| Sugar Beet Army Worm (*S. exigua*) | n/t | n/t | n/t |
| Tobacco Flea Beetle (*E. hiritipennis*) | n/t | n/t | n/t |
| Tomato Hornworm (*M. quinquemaculata*) | n/t | n/t | n/t |
| Tomato Fruit worm (*H. zea*) | n/t | n/t | n/t |
| Whitefly (*T. vaporariorum*) | n/t | n/t | n/t |
| Other | n/t | n/t | n/t |

Chemistry and Composition of Full-Ripe Fruits

TABLE 2

| Hot-break tomato juice characteristics for new variety 'H2249' and two check varieties 'H1015' and 'H3402' | | | |
| --- | --- | --- | --- |
| | 'H2249' | 'H1015' | 'H3402' |
| Serum viscosity (centistokes) | 5.3 | 7.7 | 6.6 |
| Juice Bostwick (cm) | 12.7 | 13.3 | 12.4 |
| Soluble solids (° Brix) | 5.0 | 5.3 | 5.1 |

Average of 3 years of trials in California in a total of 15 locations for H2249, 18 locations for H1015 and 23 locations for H3402.

TABLE 3

| Phenology | | | |
| --- | --- | --- | --- |
| | 'H2249' | 'H1015' | 'H3402' |
| Fruiting Season | Short | Short | Short |
| Relative Maturity | Late | Early-Mid | Mid |

TABLE 4

| Adaptation | | | |
| --- | --- | --- | --- |
| | 'H2249' | 'H1015' | 'H3402' |
| Culture | Field | Field | Field |
| Principle use | Whole Pack/ Fresh Market/ Concentrated | Whole Pack/ Concentrated | Whole Pack/ Concentrated |
| Machine harvest | Yes | Yes | Yes |
| Regions of adaptability | | | |
| California Sacramento/ upper SJ valley | No | Yes -3 | Yes -3 |
| California lower SJ valley | No | Yes -2 | Yes -2 |
| Northeastern USA | Yes -1 | Yes -1 | Yes -1 |

If more than one category applies, they are listed in rank order.

Comparison of 'H2249' to Closest Varieties

Data in Table 1 are based primarily upon trials conducted in Collegeville, California from two replications, non-staked, in a research plot environment among two checks, 'H1015' and 'H3402'. Data in Tables 2, 3, and 4 are based upon observations and laboratory fruit quality measurements made in numerous trials throughout California over a 3-year period, relative to 'H1015' and 'H3402'. Disease resistance and adaptability assessments are based upon DNA markers associated with the disease resistance when available or numerous observations collected in regions/climates with specific disease pressure, specifically for ripe fruit rots, bacterial spot, bacterial canker, early blight, and late blight, including Ontario, Canada.

Several characteristics can distinguish 'H2249' from the similar commercial variety 'H1015', particularly when compared side-by-side in trials. The most prominent distinctions between 'H2249' and 'H1015' are the later cropping cycle of 'H2249', the addition of late blight resistance and the large fruit size. From a usage standpoint, 'H2249' is a variety that can be grown for dual use markets; where fruits are harvested for both fresh market use and processing. Both 'H2249' and 'H3402' are North Eastern US adapted processing varieties. The most prominent distinguishing features between these varieties include the compact vine and large fruit size in 'H2249' as well as the addition of late blight and bacterial spot resistance.

Further Embodiments

Additional methods provided herein include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid. Accordingly, another aspect of the disclosure relates a method for producing an inbred tomato variety by: planting seed of the tomato variety 'H2249'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H2249'. Tomato plants capable of expressing substantially all of the physiological and morphological characteristics of the parental inbred lines of tomato variety 'H2249' include tomato plants obtained by chasing selfs from seed of tomato variety 'H2249'.

One of ordinary skill in the art will recognize that once a breeder has obtained inbred tomato plants by chasing selfs from seed of tomato variety 'H2249', the breeder can then produce new inbred plants such as by sib-pollinating, or by crossing one of the identified inbred tomato plant with a plant of the tomato variety 'H2249'.

The disclosure further includes introducing one or more desired traits into the tomato variety 'H2249'. For example, the desired trait may include male sterility, male fertility, herbicide resistance, insect resistance, disease resistance, and drought resistance.

The desired trait may be found on a single gene or combination of genes. The desired trait may be a genetic locus that is a dominant or recessive allele. The genetic locus may be a naturally occurring tomato gene introduced into the genome of a parent of the variety by backcrossing, a natural or induced mutation, or a transgene introduced through genetic transformation techniques. For a genetic locus introduced through transformation, the genetic locus may comprise one or more transgenes integrated at a single chromosomal location. Accordingly, the disclosure provides tomato plants or parts thereof that have been transformed with one or more transgenes (i.e., a genetic locus comprising a sequence introduced into the genome of a tomato plant by transformation) to provide a desired trait. In one aspect, the one or more transgenes are operably linked to at least one regulatory element. In one aspect, the tomato plant or plant part comprising a transgene has all the physiological and morphological characteristics of tomato variety 'H2249'.

The gene(s) may be introduced to tomato variety 'H2249' through a variety of well-known techniques, including for example, molecular biological, other genetic engineering, or plant breeding techniques, such as recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) (also referred to as Microsatellites)), enhanced selection, genetic marker enhanced selection, and transformation. Accordingly, tomato seed, plants, and parts thereof produced by such genetic engineering or plant breed techniques are also part of the present disclosure.

Also provided herein are single locus converted plants and seeds developed by backcrossing wherein essentially all of the morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus). One or more locus conversion traits may be introduced into a single tomato variety. In one aspect, the tomato plant or tomato plant part comprising a single locus conversion has all the physiological and morphological characteristics of tomato variety 'H2249'.

Deposit Information

A deposit of the tomato variety 'H2249' is maintained by HeinzSeed Company, having an address at 6755 CE Dixon St, Stockton, California 95206, United States of America. Access to this deposit will be available during the pendency of this application to persons determined by the Commissioner of Patents and Trademarks to be entitled thereto under 37 C.F.R. § 1.14 and 35 U.S.C. § 122.

At least 625 seeds of tomato variety 'H2249' were deposited on Dec. 15, 2022, according to the Budapest Treaty in the American Type Culture Collection (ATCC), P.O. Box 1549, MANASSAS, VA 20108 USA. The deposit has been assigned ATCC number PTA-127484. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposits will be maintained in the ATCC depository, which is a public depository, for a period of 30 years, or 5 years after the most recent request, or for the effective life of the patent, whichever is longer, and will be replaced if a deposit becomes nonviable during that period.

What is claimed is:

1. A plant produced by growing tomato seed designated as 'H2249', representative sample of seed having been deposited under ATCC Accession Number PTA-127484.

2. A plant part isolated from the plant of claim 1, wherein the plant part comprises at least one tomato variety 'H2249' cell.

3. The plant part of claim 2, wherein the part comprises one or more of leaf, rootstock, scion, fruit, cotyledon, meristem, root, root tip, pistil, flower, stem, calli, stalk, hypocotyl, pericarp, and portion thereof containing at least one regenerable tomato variety 'H2249 cell.

4. A tomato plant having all the physiological and morphological characteristics of a plant produced by growing tomato seed designated as 'H2249', representative sample of seed having been deposited under ATCC Accession Number PTA-127484.

5. A plant part isolated from the plant of claim 4, wherein the plant part comprises at least one tomato variety 'H2249' cell.

6. The plant part of claim 5, wherein the part comprises one or more of leaf, rootstock, scion, fruit, cotyledon, meristem, root, root tip, pistil, flower, stem, calli, stalk, hypocotyl, pericarp, and portion thereof containing at least one regenerable tomato variety 'H2249 cell.

7. A tissue culture of regenerable cells from the plant part of claim 2, wherein said tissue culture of regenerable cells has all the physiological and morphological characteristics of tomato variety 'H2249'.

8. A tomato plant regenerated from the tissue culture of claim 7, the plant having all of the physiological and morphological characteristics of tomato variety 'H2249', wherein a representative sample of seed has been deposited under ATCC Accession Number PTA-127484.

9. A protoplast produced from the tissue culture of claim 7, wherein a plant regenerated from the protoplast has all of the physiological and morphological characteristics of tomato variety 'H2249'.

10. A method of producing a progeny tomato plant of tomato variety 'H2249', the method comprising crossing the plant of claim 1 with another tomato plant to produce the progeny tomato plant.

11. The method of claim 10, further comprising harvesting seed from the progeny tomato plant.

12. The method of claim 10, further comprising crossing the progeny tomato plant with itself or another plant to produce seed from the progeny tomato plant.

13. A plant produced by growing tomato seed designated as 'H2249', representative sample of tomato seed designated as 'H2249' having been deposited under ATCC Accession Number PTA-127484, wherein the plant produced by growing tomato seed designated as 'H2249' further comprises a transgene introduced through genetic transformation of the plant, and otherwise has all the physiological and morphological characteristics of tomato variety 'H2249'.

14. A plant produced by growing tomato seed designated as 'H2249', representative sample of tomato seed designated as 'H2249' having been deposited under ATCC Accession Number PTA-127484, wherein the plant produced by growing tomato seed designated as 'H2249' further comprises a single locus conversion introduced through genetic transformation of the plant, and otherwise has all the physiological and morphological characteristics of tomato variety 'H2249'.

15. A method for producing a tomato fruit, the method comprising:

growing the tomato plant of claim 1 to produce a tomato fruit; and harvesting the tomato fruit.

16. A method for producing a tomato seed comprising:

self-pollinating the tomato plant of claim 1; and harvesting the resultant tomato seed.

17. A method of vegetatively propagating the plant of claim 1, the method comprising:

obtaining a part of the plant; and regenerating a plant from the part, wherein the regenerated plant has all of the physiological and morphological characteristics of tomato variety 'H2249'.

* * * * *